(12) United States Patent
Webster, Jr.

(10) Patent No.: US 6,198,974 B1
(45) Date of Patent: Mar. 6, 2001

(54) BI-DIRECTIONAL STEERABLE CATHETER

(75) Inventor: Wilton W. Webster, Jr., Diamond Bar, CA (US)

(73) Assignee: Cordis Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/157,055

(22) Filed: Sep. 18, 1998

Related U.S. Application Data

(63) Continuation-in-part of application No. 09/134,009, filed on Aug. 14, 1998.

(51) Int. Cl.$^7$ ............... A61N 1/05; A61B 5/04; A61M 37/00
(52) U.S. Cl. ............ 607/122; 600/374; 600/146; 604/95; 606/41
(58) Field of Search ................ 607/115, 122, 607/125; 600/373–375, 381, 146, 149, 150; 606/41; 604/95, 280–281

(56) References Cited

U.S. PATENT DOCUMENTS

| | | | |
|---|---|---|---|
| Re. 34,502 | 1/1994 | Webster, Jr. | 607/125 |
| 3,470,876 | 10/1969 | Barchilon | 128/348 |
| 3,605,725 | 9/1971 | Bentov | 128/2.05 R |
| 3,625,200 | 12/1971 | Muller | 128/2.05 R |
| 4,191,196 | 3/1980 | Bradley et al. | 128/733 |
| 4,233,991 | 11/1980 | Bradley et al. | 128/733 |
| 4,685,457 | 8/1987 | Donenfeld | 128/207.14 |
| 4,753,223 | 6/1988 | Bremer | 128/4 |
| 4,826,087 | 5/1989 | Chinery | 239/551 |
| 4,838,859 | 6/1989 | Strassmann | 604/95 |
| 4,921,482 | 5/1990 | Hammerslag et al. | 604/95 |
| 4,960,134 | 10/1990 | Webster, Jr. | 128/786 |
| 4,998,916 | 3/1991 | Hammerslag et al. | 604/95 |
| 5,019,090 | 5/1991 | Pinchuk | 606/194 |
| 5,037,391 | 8/1991 | Hammerslag et al. | 604/95 |
| 5,108,368 | 4/1992 | Hammerslag et al. | 604/95 |
| 5,318,525 | 6/1994 | West et al. | 604/95 |
| 5,368,564 | 11/1994 | Savage | 604/95 |
| 5,383,923 | 1/1995 | Webster, Jr. | 607/125 |
| 5,397,304 | 3/1995 | Truckai | 604/95 |
| 5,397,321 | 3/1995 | Houser et al. | 606/41 |
| 5,419,767 | 5/1995 | Eggers et al. | 604/114 |
| 5,431,168 | * 7/1995 | Webster, Jr. | 604/95 |
| 5,441,483 | 8/1995 | Avitall | 604/95 |
| 5,456,664 | 10/1995 | Heinzelman et al. | 604/95 |
| 5,462,527 | * 10/1995 | Stevens-Wright et al. | 604/95 |
| 5,492,119 | 2/1996 | Abrams | 128/642 |
| 5,507,725 | 4/1996 | Savage et al. | 604/95 |
| 5,588,964 | 12/1996 | Imran et al. | 604/95 |
| 5,626,136 | 5/1997 | Webster et al. | 128/642 |
| 5,643,255 | * 7/1997 | Organ | 606/41 |
| 5,656,029 | 8/1997 | Imran et al. | 604/95 |
| 5,656,030 | 8/1997 | Hunjan et al. | 604/95 |
| 5,681,280 | 10/1997 | Rusk et al. | 604/95 |

* cited by examiner

*Primary Examiner*—Jeffrey R. Jastrzab
(74) *Attorney, Agent, or Firm*—Christie, Parker & Hale, LLP

(57) ABSTRACT

A bi-directional electrode catheter comprising an elongated tubular catheter body, a catheter tip section at the distal end of the catheter body and a control handle at the proximal end of the catheter. The tip section comprises two pair of generally diametrically opposed off-axis lumens. Two pair of puller wires extend from the handle, through the catheter body, and into the off-axis pair of lumens of the tip section, where they are anchored in the tip section at different locations along the length of the tip section. Compression coils extend through the catheter body in surrounding relation to the puller wires. At their proximal ends, the puller wires are attached to movable pistons in the control handle. Each piston is controlled by an operator using a slidable button fixedly attached to each piston. Movement of selected buttons results in deflection of the tip section into a generally planar "U"- or "S"-shaped curve.

25 Claims, 7 Drawing Sheets

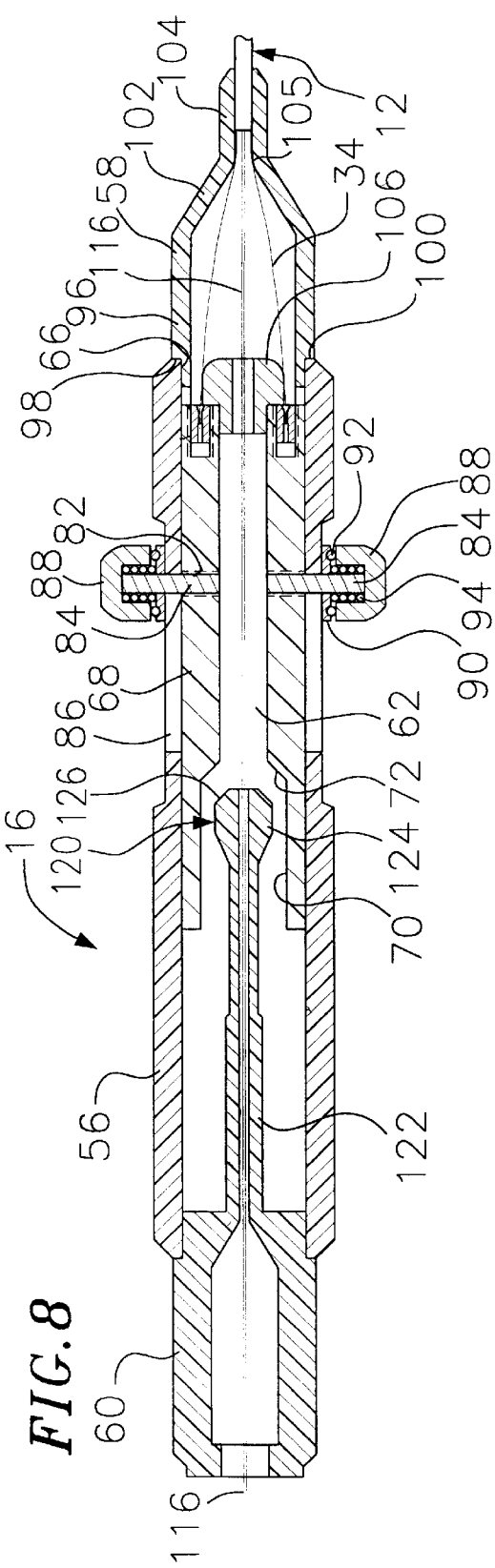
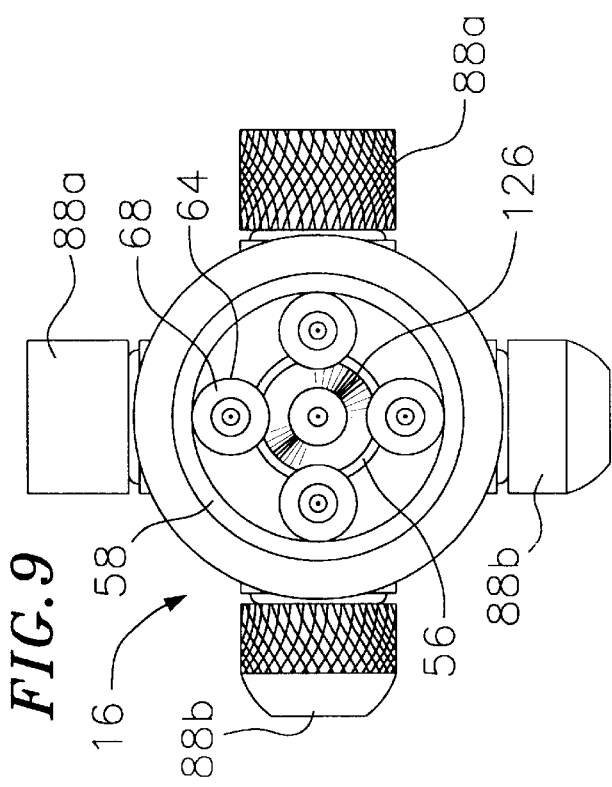
FIG. 8
FIG. 9

BI-DIRECTIONAL STEERABLE CATHETER

CROSS-REFERENCE TO RELATED APPLICATION

This application is a continuation-in-part of U.S. application Ser. No. 09/134,009, filed Aug. 14, 1998, the disclosure of which is incorporated herein by reference.

FIELD OF THE INVENTION

This invention relates to catheters having steerable tips and particularly to a catheter having a tip which is steerable in two directions.

BACKGROUND OF THE INVENTION

Steerable or deflectable tip cardiovascular catheters are useful in many applications, being a marked improvement over catheters with fixed tips. They are especially useful in the field of electrophysiology for performing radio frequency ablation of cardiac tissue to interrupt abnormal electrical pathways in the heart.

There are presently several useful designs of steerable tip catheters. One such steerable tip catheter is described in Reissue Pat. No. 34,502. The catheter has an elongated catheter body and tip portion which can be deflected into a semi-circle in one direction. In addition, the catheter body and tip portion can be rotated. Therefore by tip deflection, catheter rotation and catheter translation, i.e., lengthwise movement of the catheter, contact of the tip portion with most areas of a heart chamber may be made.

There are, however, structures and irregularity in the heart chambers which often make access to a particular location difficult. In some cases it is necessary to reach around obstacles to contact a desired site. Moreover, it may be necessary to use a longer or shorter deflectable tip portion to reach a particular site and maintain adequate stable contact.

One early multidirectional deflectable tip catheter had a catheter body and tip with 5 lumens, i.e., a central lumen and four outer lumens disposed symmetrically around the central lumen. This catheter had four puller wires which extended through the outer lumens. The distal ends of the puller wires were attached to a ring at the tip and the proximal ends were attached to a "joy stick". The central lumen was open at its distal end and connected to a luer hub at its proximal end. This catheter had no reinforcement in its body or tip. It was not suitable for electrophysiology because it had effectively no torque transmission to the tip which made tip rotation difficult. Moreover, the catheter body was subject to the same deflection as the tip, but to a lesser degree.

A more recent steerable catheter has a steerable tip that is controlled by a bendable control handle. Multiple puller wires connect the steerable tip to this control handle which can be bent in any direction and can be thought of as a multiple ball joint with friction. The tip, once deflected, can be further deflected laterally by an internal stylette. The disadvantage of this catheter design is that the tip is very soft and has poor lateral stiffness due to the presence of the stylette which cannot transmit torque effectively. Because of this, an electrode at the tip of the catheter cannot be held firmly against the myocardial wall.

Another recent steerable tip catheter comprises a deflectable tip which can be deflected in one direction by a puller wire and further deflected laterally by an internal stylette. The stylette can also be moved axially within the catheter to change the shape of the tip curvature.

The disadvantage of this catheter design is that the lateral stiffness of the tip is dependent upon the stylette which cannot transmit torque effectively.

In a design wherein the tip is rotated by means of a stylette, it follows that the lateral stiffness of the tip must be less than that of the stylette alone. This is because some torque from the stylette is required to rotate the tip. Moreover, the stylet must be kept small to allow the catheter body and tip to bend and to be safe within the patient body and heart.

SUMMARY OF THE INVENTION

The present invention provides a cardiovascular catheter comprising a steerable catheter tip section, an elongated catheter body and a control handle. The catheter tip section comprises at least two generally diametrically opposed off-axis lumens, and preferably an axial lumen.

The catheter body comprises at least one lumen in communication with the off-axis lumens of the catheter tip section. Preferably, the catheter body comprises a single central lumen in communication with each of the off-axis lumens in the catheter tip section.

The catheter comprises two pairs of elongated puller wires which extend through the lumen(s) of the catheter body and into the off-axis lumens in the catheter tip section. One pair of puller wires extends into one off-axis lumen or lumen pair of the tip section and the other puller wire pair extends into the diametrically opposed off axis lumen or lumen pair in the tip section. The distal ends of the puller wires are anchored to the tip section. Each pair of puller wires comprises a long and a short puller wire, the short puller wire of the pair being anchored at a location within the tip section proximal to the anchor location of the long puller wire of the pair. A compression coil extends through the catheter body in surrounding relation to each puller wire for resisting compression forces on the catheter body when a puller wire is moved in a proximal direction relative to the catheter body. The proximal end of each compression coil is fixedly attached to the proximal end of the catheter body, and the distal end of the compression coil is fixedly attached to the distal end of the catheter body and/or at a selected location along the length of the catheter tip section. The site of attachment of the distal end of the compression coil and the anchor site of the puller wire associated with that compression coil in the tip section determine the length of the tip deflection curvature in the direction of that puller wire.

Longitudinal movement of the puller wires and hence deflection of the tip section is accomplished by means of the control handle. A preferred control handle comprises a handle body having four movable, preferably slidable, members. Each movable member is connected to a puller wire so that movement, preferably in a proximal direction, of a movable member from a first position towards a second position results in proximal movement of the puller wire associated with that member with respect to the catheter body and deflection of the tip section in the direction of the off-axis lumen containing that puller wire.

In a preferred embodiment, the long puller wire from each pair of puller wires is anchored at a first location adjacent to the distal end of the tip section, preferably anchored to a tip electrode. The short puller wire from each pair is anchored to the side wall of the tip section at a second location spaced-apart proximally from the distal end of the tip section, preferably at about the mid-point of the tip section. The distal ends of the compression coils surrounding the short puller wires are fixedly attached to either the distal end of the catheter body or the proximal end of the tip section. The distal ends of the compression coils surrounding the long puller wires are also fixedly attached to either the distal end of the catheter body or the proximal end of the tip section. Alternatively, the distal ends of the compression coils surrounding the long puller wires are attached to the tip section at a position adjacent the anchor sites of the short puller wire the tip section adjacent the second location.

Proximal movement of a short puller wire of the pair of puller wires results in a first curve in the direction of that short puller wire between the distal end of the compression coil surrounding that puller wire, e.g, the distal end of the catheter body and the location where the puller wire is anchored. Proximal movement of the long puller wire of the same pair will result in a continuation of that curve resulting in the deflection of the tip section into a generally planar. Alternatively, proximal movement of the long puller wire of the diametrically opposite pair of puller wires results in a second curve in a direction opposite the first curve from the distal end of the compression coil surrounding that puller wire, i.e., the second location, and the distal end of the catheter tip section. The result is a generally planar "S" shaped curve.

In another preferred embodiment of the invention, the tip section comprises an axial lumen in addition to the off-axis lumen. In the proximal portion of the tip section, the two long puller wires extend into the axial lumen while the two short puller wires extend into the off axis lumens. At a position adjacent or distal to the anchor sites of the short puller wires, the long puller wires pass into the off axis lumens of their associated short puller wires and are anchored at positions distal to the anchor sites of the short puller wire and preferably adjacent the distal end of the tip section. In this arrangement, proximal movement of a long puller wire deflects only the portion of the tip section where it extends through the off axis lumen, i.e., the distal portion of the tip section. Deflection of the proximal portion of the tip section results from proximal movement of a short puller wire.

It is understood that an additional lumen may be provided for passage of other compounds. For example, in an electrophysiology catheter, an additional lumen may serve to carry electrode lead wires. In other instances the additional lumen may be open at its distal end to conduct fluids into or out of the catheter. It may also serve to conduct other energy delivery devices such as an optical fiber, to carry a fiber optic bundle for direct viewing, to inflate a balloon, to serve as a conduit for needles and the like or other useful interventions.

BRIEF DESCRIPTION OF THE DRAWINGS

These and other features and advantages of the present invention will be better understood by reference to the following detailed description when considered in conjunction with the accompanying drawings wherein:

FIG. 4a is a longitudinal cross-section of the catheter tip section showing a preferred means for anchoring the long puller wires 34a.

FIG. 8 is a longitudinal cross-sectional view of a preferred control handle.

FIG. 9 is an end view of the control handle of FIG. 8 with the proximal cap and insert.

DETAILED DESCRIPTION

Figure 1:
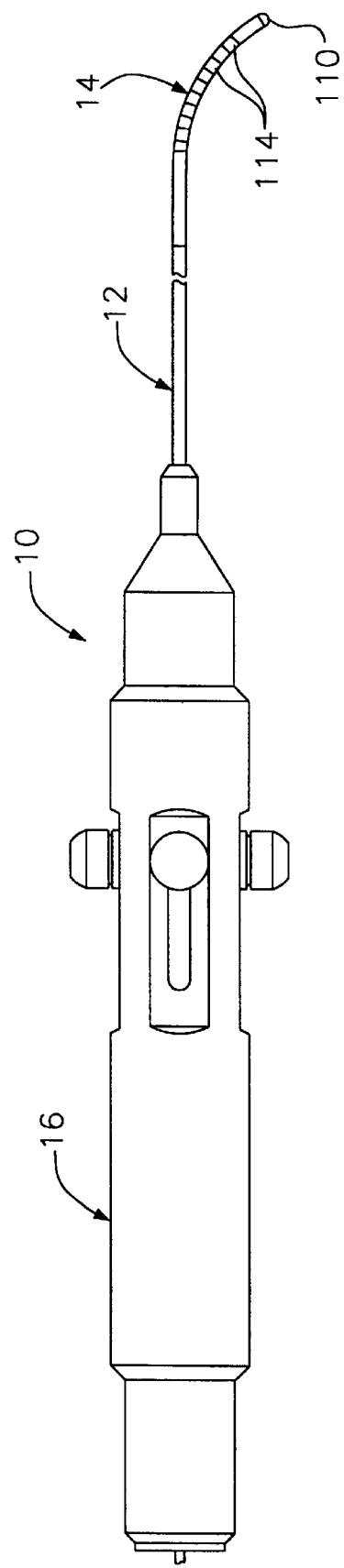
FIG. 1 is side view showing a preferred bi-directional catheter constructed in accordance with the present invention.

A particularly preferred deflectable electrode catheter constructed in accordance with the present invention is shown in FIGS. 1 to 10. The catheter 10 comprises an elongated catheter body 12, a deflectable tip section 14 and a control handle 16.

The catheter body 12 comprises an elongated tubular construction having a single central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter may vary according to the application. A presently preferred catheter has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide. The stiffening tube 22, along with the braided outer wall 20, provides improved torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter has an outer diameter of about 0.092 inch and a lumen diameter of about 0.052 inch.

Figure 4A:
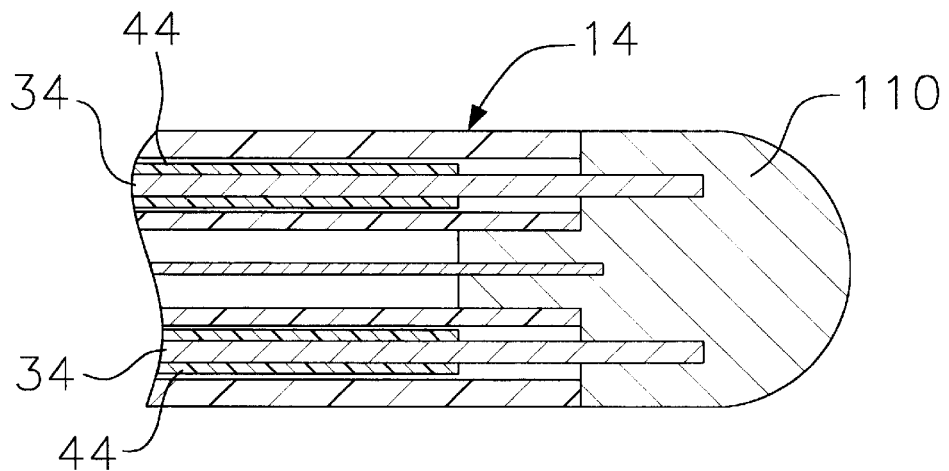
Figure 4B:
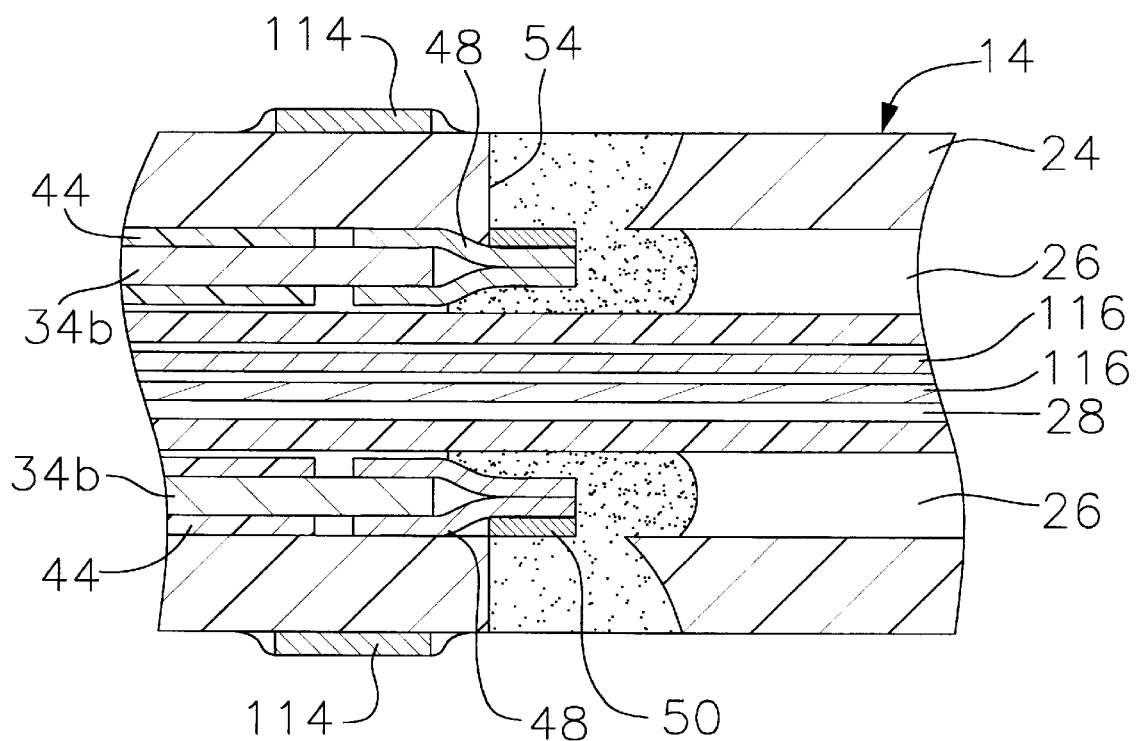
FIG. 4b is a longitudinal cross-sectional view of the catheter tip section showing another preferred means for anchoring the long or short puller wire 34b.
Figure 5:
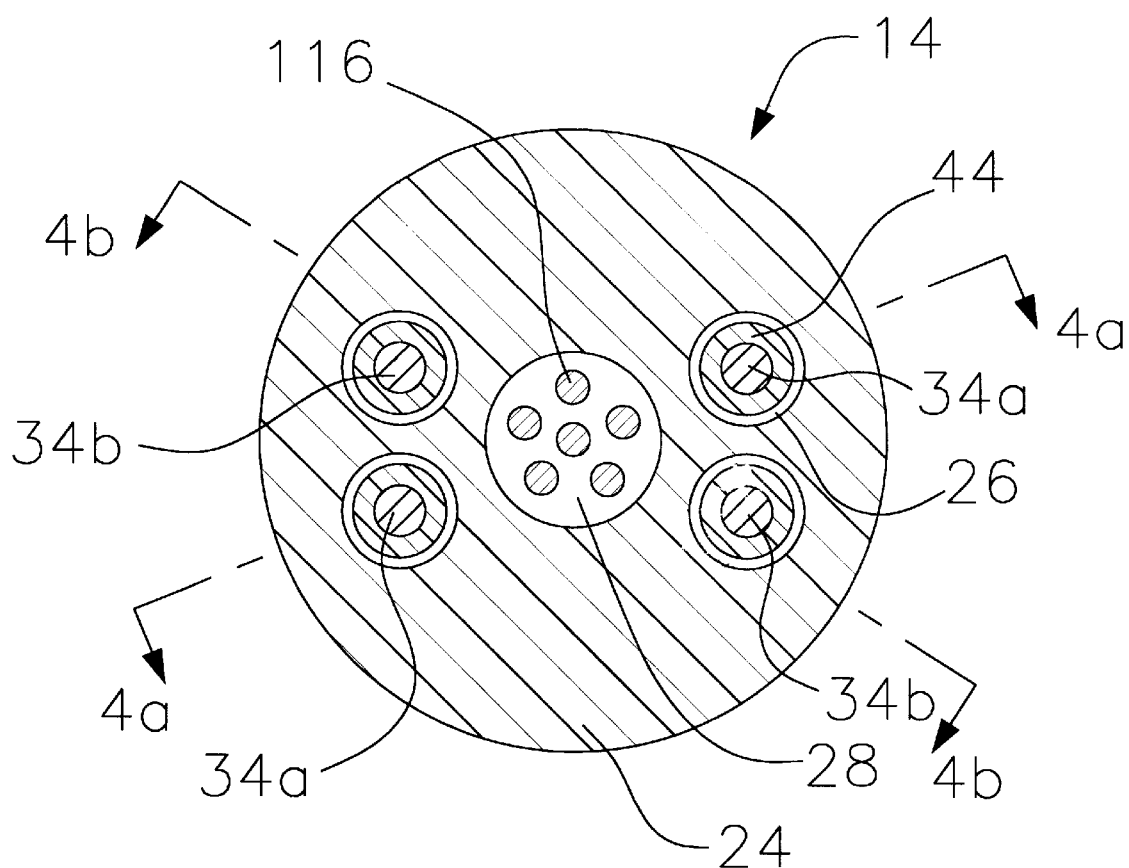
FIG. 5 is a transverse cross-sectional view of the catheter tip section of FIG. 4 taken along line 5—5.

As shown in FIGS. 4 and 5, the tip section 14 comprises a short section of tubing 24 having four outer off-axis lumens 26 and a central axial lumen 28. The off-axis lumens 26 are arranged in two pairs, the pairs extending through diametrically-opposed quadrants of the tip section. The lumens of each pair are preferably as close together as practical.

The tubing 24 is made of a suitable non-toxic material that is preferably more flexible than the catheter body 12. A presently preferred material for the tubing 24 is braided polyurethane, i.e., polyurethane with an embedded mesh of braided stainless steel or the like.

The outer diameter of the tip section 14, like that of the catheter body 12, is preferably no greater than about 8 french. The off-axis lumens 26 each have a diameter preferably of about 0.018–0.020 inch. An axial or central lumen 28 is provided which preferably has a diameter of about 0.020–0.025 inch.

Figure 2:
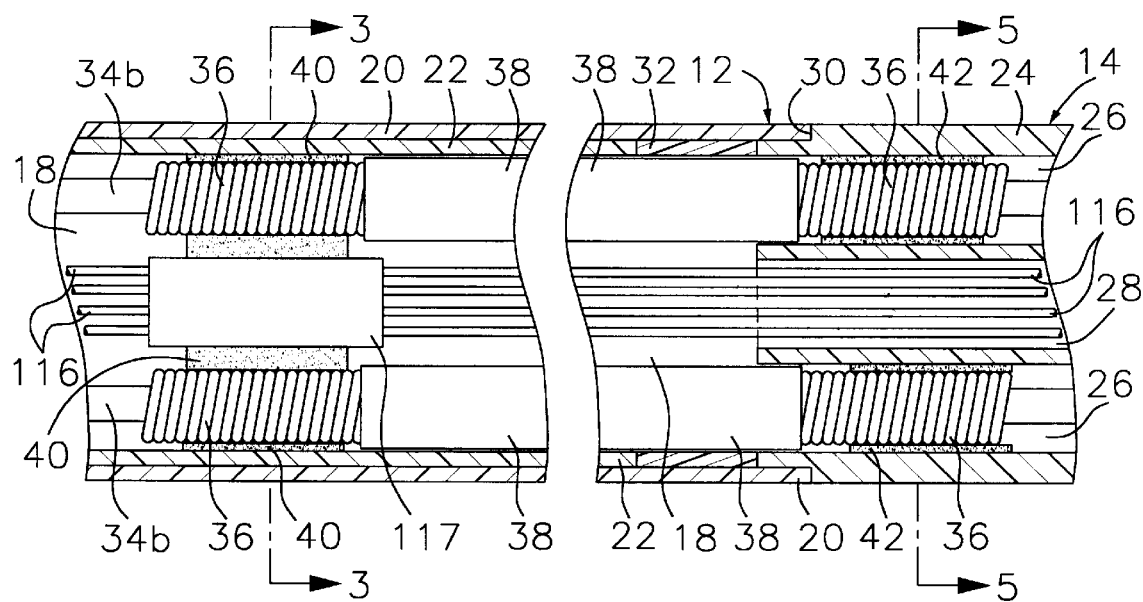
FIG. 2 is a longitudinal cross-sectional view of one embodiment of a catheter body of a catheter according to the present invention, including the junction between the catheter body and tip section.
Figure 3:
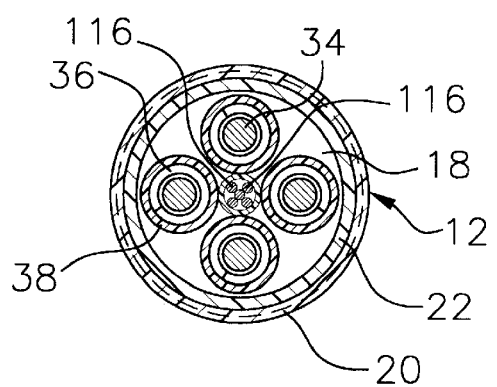
FIG. 3 is a transverse cross-sectional view of the catheter body of FIG. 2 taken along line 3—3.

A preferred means for attaching the catheter body 12 to the tip section 14 is illustrated in FIG. 2. The proximal end of the tip section 14 comprises an outer circumferential notch 30 that receives the inner surface of the outer wall 20 of the catheter body 12. The tip section 14 and catheter body 12 are attached by glue or the like.

In the arrangement shown, a spacer 32 lies within the catheter body 12 between the distal end of the stiffening tube 22 and the proximal end of the tip section 14. The spacer 32 is preferably made of a material that is stiffer than the material of the tip section 14, e.g., polyurethane, but not as stiff as the material of the stiffening tube 22, e.g., polyimide. A spacer made of Teflon® is presently preferred. A preferred spacer 32 has a length of from about 0.25 inch to about 0.75 inch, more preferably about 0.50 inch. Preferably the spacer 32 has an outer and inner diameter about the same as the outer and inner diameters of the stiffening tube 22. The spacer 32 provides a transition in flexibility at the junction of the catheter body 12 and the tip section 14 to bend smoothly without folding or kinking.

In the embodiment shown the distal end of the tip section 14 carries a tip electrode 110. Mounted along the length of the tip section 14 are a plurality of ring electrodes 114. The length of each ring electrode 114 is not critical, but is preferably about 1 mm to about 4 mm. The ring electrodes 114 are spaced apart, preferably at a distance of about 2 mm to about 4 mm.

The tip electrode 110 and ring electrodes 114 are each connected to a separate lead wire 116. Each lead wire 116 extends through the axial lumen 28 in the tip section 14, through the central lumen 18 in the catheter body 12 and through the control handle 16. The proximal end of each lead wire 116 extends out the proximal end of the control handle 16 and is connected to an appropriate jack or other connector, which can be plugged into or otherwise connected to a suitable monitor, source of energy, etc. If desired, the portion of the lead wires 116 extending through the catheter body 12 may be enclosed or bundled within a non-conductive protective tube or sheath.

The lead wires 116 are connected to the tip electrode 110 and ring electrode 114 by any conventional technique. Connection of a lead wire 116 to the tip electrode 110 is preferably accomplished by weld. Connection of a lead wire 116 to a ring electrode 114 is preferably accomplished by first making a small hole through the tubing 24. Such a hole can be created, for example, by inserting a needle through the tubing 24 and heating the needle sufficiently to form a permanent hole. A lead wire 116 is then drawn through the hole by using a microhook or the like. The end of the lead wire 116 is then stripped of any coating and welded to the underside of the ring electrode 114, which is then slid into position over the hole and fixed in place with polyurethane glue or the like.

The catheter comprises two pair of puller wires 34. Each pair of puller wires 34 extends from the control handle 16, through the central lumen 18 in the catheter body 12 and into one of the pairs of off-axis lumens 26 of the tip section 14. As described in more detail below, the proximal end of each puller wire 34 is anchored within the control handle 16 and the distal end of each puller wire 34 is anchored within the tip section 14.

Each puller wire 34 is made of any suitable metal, such as stainless steel or Nitinol. Preferably each puller wire 34 is coated with coating, such as a coating of Teflon®, or the like. Each puller wire 34 has a diameter preferably ranging from about 0.006 inch to about 0.0010 inch. Preferably all of the pullers 34 have the same diameter.

In the embodiment shown, each puller wire 34 pair comprises a "long" and a "short" puller wire 34. The long puller wire 34a of each puller wire pair is anchored at the distal end of the tip section 14. The short puller wire 34b of each puller wire pair is anchored to the side wall of the tip section 14 at about the midpoint of the tip section. It is preferred that the short puller wire 34b of each puller wire pair are anchored at about the same position, i.e., the same distance from the distal end of the tip section 14 and the long puller wire 34a of each puller wire pair are anchored at the distal end of the tip section 14. It is understood, however, that the anchor positions of the puller wires may be varied as desired. The two long puller wires 34a can be anchored either to the tip electrode 110 with weld or the like, as shown in FIG. 4a, or to the side wall of the tip section 14.

Figure 6:
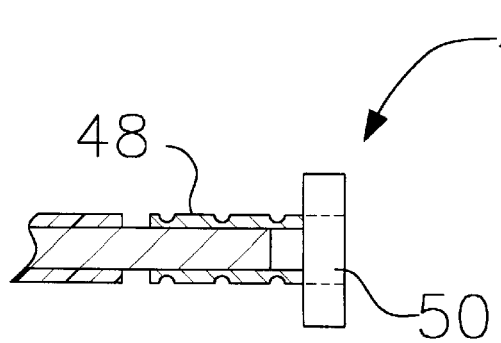
FIG. 6 is a longitudinal cross-sectional view of a preferred puller wire T-bar anchor.
Figure 7:
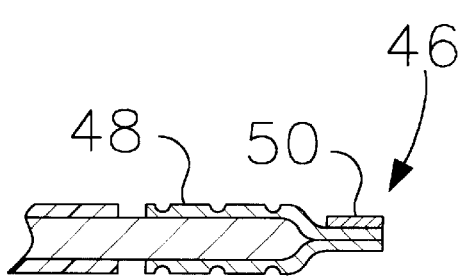
FIG. 7 is a longitudinal cross-sectional view of the puller wire T-bar anchor of FIG. 4 rotated 90° to show the cross-piece on end.

If attached to the side wall of the tip section 14, each puller wire 34 is preferably attached by means of an anchor 46 fixedly attached to the distal end of the puller wire 34, as illustrated in FIGS. 4b, 6 and 7. In such an embodiment, the anchor 46 is formed by a metal tube 48, e.g., a short segment of hypodermic stock, that is fixedly attached, e.g., by crimping, to the distal end of the puller wire 34. The tube 48 has a section that extends a short distance beyond the distal end of the puller wire 34. A cross-piece 50 made of a small section of stainless steel ribbon or the like is soldered or welded in a transverse arrangement to the distal end of the metal tube 48, which is flattened during the operation. This creates a T-bar anchor 52. A notch 54 is created in the side of the tip section 14 resulting in an opening in the off-axis lumen 26 carrying the puller wire 34. The cross piece 50 lies transversely within the notch 54. Because the length of the ribbon forming the cross-piece 50 is longer than the diameter of the opening into the off-axis lumen 26, the anchor 46 cannot be pulled completely into the off-axis lumen. The notch 54 is then sealed with polyurethane glue or the like to give a smooth outer surface. The glue flows into the off-axis lumen to fully secure the anchor. Other means for anchoring the puller wires 34 in the tip section 14 would be recognized by those skilled in the art and are included within the scope of the invention.

The catheter further comprises four compression coils 36 in surrounding relation to the puller wires 34. Each compression coil 36 is made of any suitable metal, such as stainless steel. Each compression coil 36 is tightly wound on itself to provide flexibility, i.e., bending, but to resist compression. The inner diameter of each compression coil 36 is preferably slightly larger than the diameter of its associated puller wire 34. For example, when a puller wire 34 has a diameter of about 0.007 inch, the corresponding compression coil 36 preferably has an inner diameter of about 0.009 inch. The coating on the puller wires 34 allows them to slide freely within the compression coils 36. The outer surface of each compression coil 36 is preferably covered along most of its length by a flexible, non-conductive sheath 38 to prevent contact between the compression coil 36 and any wires, fibers or cables also dispersed within the central lumen 18. A non-conductive sheath 38 made of polyimide tubing is presently preferred.

Each compression coil 36 is anchored at its proximal end to the proximal end of the stiffening tube 22 in catheter body 12 by a glue joint 40. When a stiffening tube 22 is not used, each compression coil is anchored directly to the outer wall 20 of the catheter body 12. A transfer tube 117 extends through the glue joint 40. The transfer tube 117 provides a tunnel through which the electrode lead wires 116 extend and allows the electrode lead wires 116 longitudinal movement through the glue joint.

The distal ends of the compression coils 36 may extend into the off-axis lumens of the tip section and are anchored at their distal ends to the proximal end of the tip section 14 by a glue joint. Alternatively, the distal ends of the two compression coils 36 can be anchored to the distal end of the stiffening tube 22 in the catheter body 12 or directly to the distal end of the outer wall 20 of the catheter body 12 when no stiffening tube 22 is used. In the latter arrangement, a second transfer tube 117 is provided through the glue joint 42 to provide slidable passage of the electrode lead wires 116 from the central lumen of the catheter body into the central lumen of the tip section.

Both glue joints 40, 42 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 and the stiffening tube 22 that is heated sufficiently to form a permanent hole. The glue is then introduced through the hole to the outer surface of the compression coil 36 and wicks around the outer circumference to form a glue joint about the entire circumference of the compression coil 36.

Within the off-axis lumens 26, each puller wire 34 is surrounded by a plastic sheath 44, preferably made of Teflon®. The plastic sheathes 44 prevent the puller wires 34 from cutting into the wall of the tip section 14 when the tip section is deflected. Alternatively, each puller wire 34 can be surrounded by a compression coil where the turns are expanded longitudinally, such that the surrounding compression coil is both bendable and compressible.

In the arrangement described above, longitudinal movement of one of the short puller wire 34b in a proximal direction result in deflection of the tip section in the direction of the off axis lumen containing that puller wire 34. Deflection occurs between the distal end of the compression coil surrounding the puller wire 34 and the anchor site of that puller wire 34. In the preferred embodiment described above, proximal movement of a short puller wire 34b results in deflection over the proximal half of the tip section in the direction of that short puller wire 34b. Thereafter, longitudinal movement of one of the long puller wires 34a results in deflection of the distal half of the tip section in the direction of that long puller wire 34a.

It has been found that if the tip is deflected by means of a short puller wire 34b first, subsequent deflection by means of a long puller wire 34a is generally limited to the portion of the tip section beyond the anchor site of the short puller wire 34b and does not substantially affect the amount of deflection which occurs as a result of movement by the short puller wire 34b. If the long puller wire 34a that is moved is adjacent the short puller wire 34b which was moved first, the tip will be deflected into a generally planar "U" shape, the degree of curvature being generally consistent along the length of the curve. If the long puller wire 34a that is moved is in an off-axis lumen diametrically opposed to the short puller wire 34b which was moved, the tip section will be deflected into a generally planar "S" shape.

It should be understood that, if desired, proximal movement of one of the long puller wires 34a may occur first followed by proximal movement of a short puller wire 34b. This sequence is not preferred because the shape and degree of curvature is not as easily controlled. For example, manipulation of a long puller wire 34a first results in deflection of the tip section over the full length of the tip section. Thereafter, proximal movement of an adjacent short puller wire 34b tends to increase the degree of curvature along the proximal half of the tip section, so that the degree of curvature is not consistent over the full length of the curve. If it is an opposite short puller wire 34b that is moved proximally, the proximal half of the tip section straightens and will reverse its curvature into an S-shape, however, a uniform degree of curvature of each curve in the "S" tends to be difficult to achieve.

In another preferred embodiment of the invention, the compression coils 36 surrounding the two short puller wire 34b are anchored at the distal end of the catheter body or proximal end of the tip section 14 as described above. In this embodiment, however, the compression coils 36 surrounding the long puller wires 34a, are anchored at about the same position along the length of the tip section as the anchor sites of the short puller wires 34b. In this arrangement, proximal movement of a long puller wire 34a can only result in deflection of the distal portion of the tip section. Hence, in this embodiment, the sequence in which the puller wires 34 are manipulated does not matter, i.e., it does not matter whether a long or short puller wire 34b is moved proximally first. It is understood that the anchor sites for the puller wires 34 may be independently varied as desired.

Figure 11:
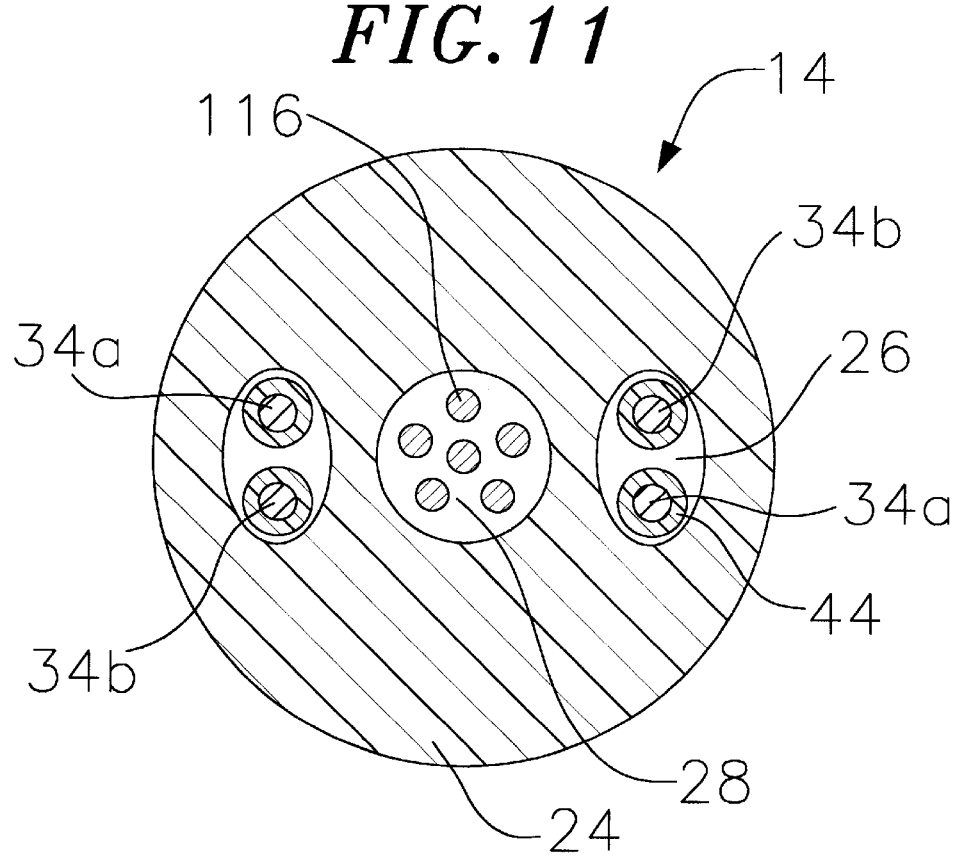
FIG. 11 is a transverse cross-sectional view of the tip section of another preferred embodiment of the invention.

An alternate embodiment having a tip section 14 with only two off-axis lumens 26 is illustrated in FIG. 11. The off-axis lumens 26, which may be oval or round as desired, are on a diametrically opposed sides of the on-axis lumen 28. A pair of adjacent puller wires 34, as described above, is contained within each off-axis lumen 26. Thus, within one off-axis lumen 26, the short puller wire 34b of a pair is anchored within the tip section 14 proximal to its adjacent long puller wire 34a. In such an embodiment, a transfer tube is provided through the glue joint which is formed at the anchor site of the short puller wire 34b. The long puller wire 34a slidably passes through the transfer tube. Alternatively, the compression coil surrounding the long puller wire 34a may extend to the anchor site of the short puller wire 34b and be anchored by the same glue as anchors the short puller wire 34b. Within the off-axis lumen 26, the adjacent puller wires 34 are preferably situated next to each other the same distance from the on-axis lumen 28.

Figure 12:
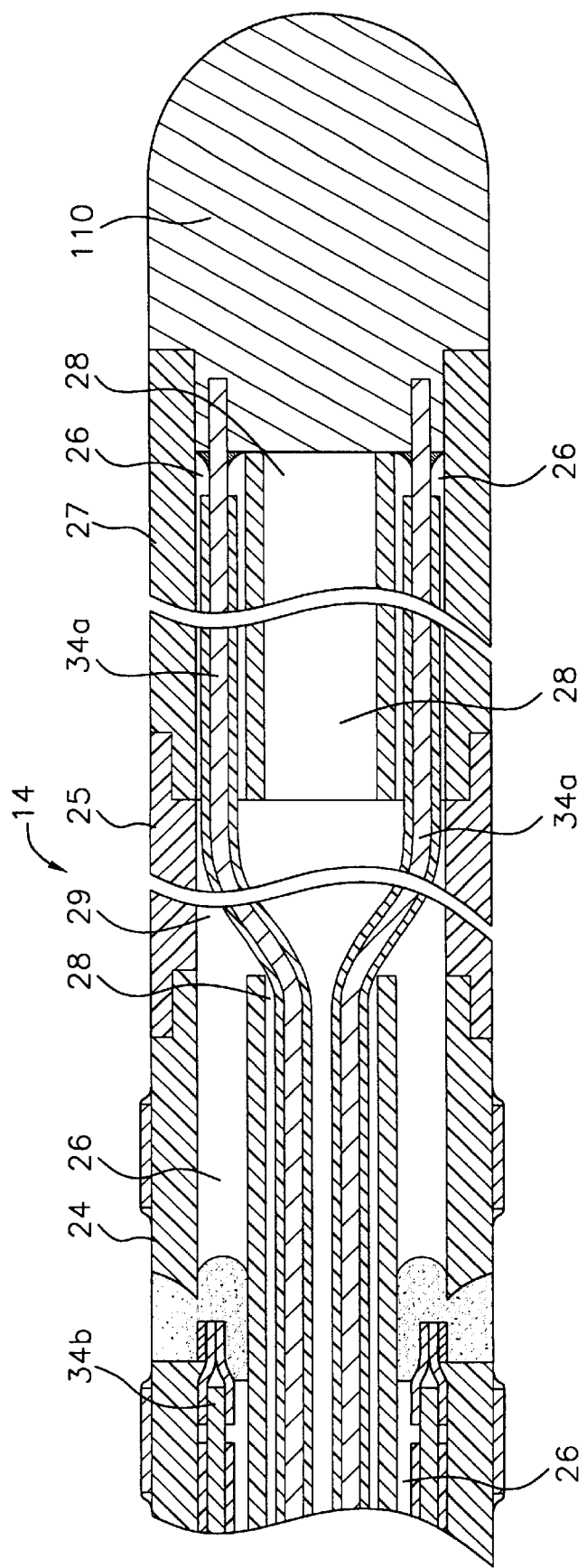
FIG. 12 is a longitudinal cross-sectional view of the tip section of yet another preferred embodiment of the invention.

With reference to FIG. 12, in another embodiment of the invention, the tip section comprises a first short section of flexible tubing 24, a bridging tube 25, a second short section of flexible tubing 27, and a tip electrode 110. The first and second short sections of flexible tubing 24 and 27 and the bridging tube can be made of any suitable material, for example, polyurethane. The first section of flexible tubing 24 contains an axial lumen 28 and two generally diametrically-opposed off-axis lumens 26. The second section of flexible tubing 27 contains two generally diametrically-opposed off-axis lumens 26 and may contain an axial lumen 28 if desired. The bridging tube 25 is generally hollow having an open interior region 29.

Each long puller wire 34a extends through an axial lumen 28 in the proximal portion of first flexible tubing 24, through the open interior region 29 of the bridging tube 25, and then into a different off-axis lumen 26 in the second section of tubing 27. In the embodiment shown, the distal ends of the long puller wires 34a are anchored, e.g., by solder or the like to a tip electrode 110. Other means for anchoring the distal ends of the long puller wires 34a to a tip electrode 110, or the distal end of the tubing 24 of the tip section 14 may be used as is well known in the art. In the catheter body 12, the long and short puller wires 34a and 34b extend through compression coils 36, the distal ends of which are fixedly attached to the distal end of the catheter body 12 or proximal end of the tip section 14 generally as described above.

By virtue of extending through an axial lumen in the proximal portion of the tip section, i.e., in the first section of tubing 24, proximal movement of a long puller wire 34a will not result in deflection of that portion of the tip section. However, because the long puller wires 34a extend through off axis lumens in the distal portion of the tip section, i.e., in the section of tubing 27, proximal movement of a long puller wire 34a will result in deflection of the distal portion of the tip section in the direction of the off axis lumen 26 through which that long puller wire 34a extends. In this embodiment, it does not matter which puller wire 34, i.e., long or short, is manipulated first.

In the embodiment shown in FIG. 12, one or more additional off axis lumens may be provided through which additional components, e.g., electrode leadwires, infusion tube, optic fiber, etc., may extend.

In each of the above embodiments, longitudinal movement of the puller wires 34 is controlled by the control handle 16. With reference to FIGS. 8 and 9, a preferred control handle 16 comprises a generally cylindrical control handle body 56, a distal cap 58 at the distal end of the control handle body 56, and a proximal cap 60 at its proximal end. The control handle body 56 comprises a cylindrical central lumen 62 and four cylindrical outer lumens 64 that overlap with, and thus communicate with, the central lumen 62.

Four pistons 68, each comprising a movable member, are slidably mounted within each of the outer lumens 64 in the control handle 16. Each piston 68 is generally cylindrical along about two-thirds of its length. The proximal third of each piston 68 is generally semi-circular in cross-section, having a flat surface 70 facing the axis of the control handle 12. At the transition between the distal cylindrical portion and the proximal semi-cylindrical portion of the piston 68, there is an angled, generally flat face 72. A preferred angle is about 45°.

Figure 10:
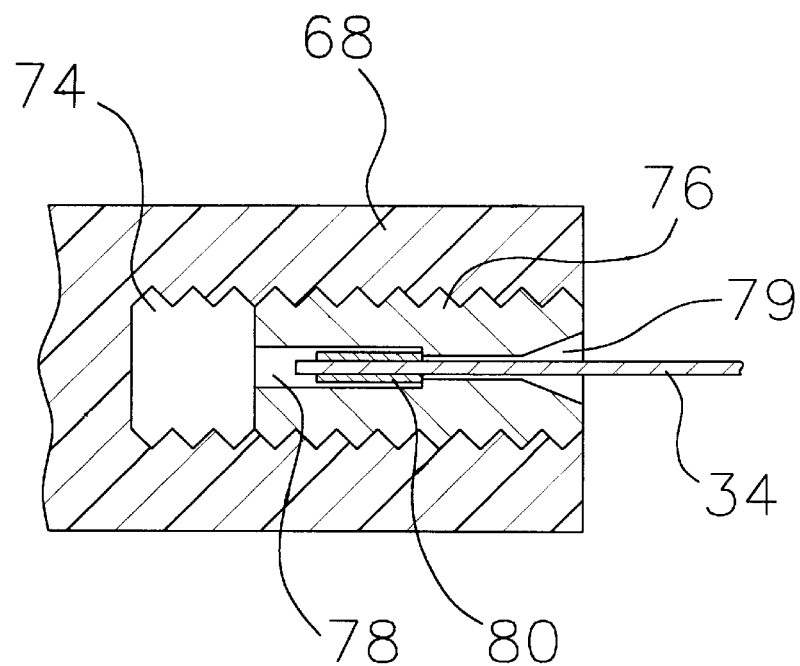
FIG. 10 is a transverse cross-sectional view of a preferred means for securing the puller wire 34 to the control handle.

With reference to FIG. 10, at the distal end of each piston 68, there is a threaded axial hold 74 that receives a threaded set screw 76. Each set screw 76 has an axial bore 78 therethrough for passage of the proximal end of one of the puller wires 34. In a preferred embodiment, the axial bore 78 has a distal section with a diameter slightly larger than the diameter of the puller wire 34 and a proximal section with a diameter larger than that of the distal section. The entrance 79 to the axial bore 78 is beveled.

Each puller wire 34 extends through the axial bore 78 of the corresponding set screw 76 and is anchored thereto. A preferred means for anchoring a puller wire 34 to a set screw 76 comprises fixedly attaching, e.g., by crimping, a short piece of hypodermic stock 80 to the proximal end of the puller wire 34 after it has passed through the distal section of the axial bore 78 of the set screw 76. The hypodermic stock 80 has a diameter greater than the diameter of the distal section of the axial bore 78 and prevents the puller wire 34 from being pulled through the axial bore 78 and out of the set screw 76. Alternatively, a cross-member, e.g., stainless-steel ribbon, may be welded to the proximal end of the puller wire 34 such that the cross-member prevents the puller wire 34 from being pulled through the axial bore of the set screw. It is understood than any other mechanism for attaching the proximal end of each puller wire 34 to one of the pistons may also be used.

Along the length of each piston 68, there is provided a threaded radial hole 82 into which a threaded post 84 is screwed. The post 84 extends radially outwardly from the axis of the control handle 16 through a longitudinal slot 86 in the control handle body 56. At the end of each post 64, remote from the respective piston 68, there is fixedly attached a button 88. This configuration completes a functional moveable member. In this arrangement, the movable member is slidably adjustable between multiple positions defined by the length of each longitudinal slot 86.

An operator may grip the outer surface of the control handle body 56 and slide a button 88 and corresponding piston 68 longitudinally along the length of the slot 86 by means of thumb pressure. The buttons 88 are preferably designed so that two buttons 88a, which correspond to two adjacent puller wires 34, are similarly shaped. Similarly the other two buttons 88b, corresponding to the other two adjacent puller wires 34, are also similarly shaped.

In a particularly preferred embodiment, as shown in FIG. 9, the buttons 88 are further differentiated, e.g., by size, texture, etc., to provide a tactile identification of the puller wire 34 that is being manipulated, e.g., which puller wire 34 pair it is associated with and whether it is the short puller wire 34b or the long puller wire 34a. For example, the buttons 88 associated with one pair may be rounded and those associated with the other pair may be cylindrical with the button associated with the short puller wires 34b being knurled while the buttons 88 associated with the long puller wires 34a being smooth. This design helps avoid confusion by a physician manipulating the catheter 10 during a medical procedure.

In a preferred embodiment, there is provided a means for adjusting the amount of manual pressure required to slide a button 88 along the length of the slot 86. For example, one physician may desire a control handle having a "light touch," i.e., requiring only a small amount of pressure to slide the buttons 88 and hence making deflection off the tip section 14 very responsive to the physician's touch. Another may prefer that substantial pressure be required to slide the buttons 88 so that the tip curvature will remain when a button 88 is released.

With reference to FIG. 8, a preferred button arrangement comprises a washer 90 and an O-ring 92 positioned between the button 88 and the control handle body 56 and a compression spring 94 in surrounding relation to the threaded post 84 between the button 88 and the washer 90. In this arrangement, rotation of a button 88 in one direction causes the threaded post 84 to thread into the radial hole 82 of the piston 68, increasing the spring force and O-ring force pressing the washer 90 against the control handle body 56. This increases the amount of frictional force that must be overcome to slide a button 88 along the length of the slot 86. Rotation of a button 88 in the opposite direction lessens such forces.

The distal cap 58 comprises a cylindrical portion 96 having a circumferential notch 98 at its proximal end. The circumferential notch 98 mates with the cylindrical flange 66 of the control handle body 56. That is, the outer diameter of the circumferential notch 98 is about the same as the inner diameter of the flange 66 of the control handle body 56. The distal cap 58 is then press-fit into the control handle body 56 until the distal edge of the flange 66 engages a shoulder 100 of the distal cap 58. Distal to the cylindrical portion 96, the distal cap 58 comprises a generally conical portion 102. A small extension 104 projects distally at the distal end of the conical portion 102. The extension 104 comprises an axial hole through which the catheter body 12 extends. The catheter body 12 is fixedly attached within the extension 104, e.g., by glue or the like.

Each of the puller wires 34 passes out of the proximal end of the catheter body 12 and extends through the distal cap 58 of the control handle 16 to a separate piston 68 within the control handle body 56. The proximal ends of the puller wires 34 are fixed to the pistons 68, e.g., by means of the set screws 76 described above. In this arrangement, longitudinal movement of a piston 68 by means of pressure on the associated button 88 longitudinally moves the puller wire 34 associated with that piston 88 and deflects the tip section 14 in a direction corresponding to the side of the tip section to which that puller wire 34 is anchored.

To assure that the puller wires 34 transition smoothly from the catheter body 12 to their anchor sites on the pistons 68, the puller wires 34 exit the distal cap 58 around a first radius and then around a second radius before entering the piston 68. The first radius is the curved inner surface 105 of the hole in the distal cap 58. The second radius is the curved surface of insert 106 that seats into the distal end of the central lumen 62 of the control handle 16. The insert 106 comprises a rounded head portion having an outer surface adjacent the distal ends of the pistons 68. The puller wires 34 pass from the catheter body 12, into the hole in the distal cap 58, around the head portion of the insert 106, and then to the corresponding pistons 68. The rounded head of the insert 106 assures that the puller wires 34 are generally co-axial with the pistons 68 at their points of attachment. This, in turn, avoids any sharp bends in the puller wires 34 at the points of attachment that could lead to weakening and potential breakage.

It is desirable to prevent simultaneous movement of the two long puller wires 34a or the two short puller wires 34b and yet allow for simultaneous movement of a combination of a long puller wire 34a and a short puller wire 34b, whether or not they are adjacent. This is accomplished by attaching the two long puller wires 34a to diametrically opposed pistons 68 in the control handle 16 and similarly attaching the two short puller wires 34b to the other diametrically opposed pistons 68. A deflectable stop 120 is provided within the control handle 16. The stop 120 comprises a central post 122 extending distally from the proximal cap 60 to a point adjacent the angled faces 72 of the pistons 68. At the distal end of the post 122, there is an enlarged head 124 having a conical surface 126 angled in a manner similar to the faces 72 of the pistons 68. The post 122 comprises an axial bore through which the electrode lead wires 116 may pass.

When one piston 68 is moved proximally, the angled face 72 of that piston engages the conical surface 126 of the head 124 of the stop 120 causing the post 122 and head 124 to move off axis. If one attempts to move the diametrically opposed piston 68 proximately, the conical surface 126 of the head 124 will engage the angled face 72 surface of that piston and prevent proximal movement. This is because, by virtue of the position of the first piston, the post 122 and head 124 cannot move out of the way of the second piston. Thus, the stop 120 allows only one piston 68 of each pair of diametrically opposed pistons to be moved at one time.

Depending on the intended use of the catheter 10, it can further comprise additional features such as temperature sensing means, an optic fiber, an infusion tube, and/or an electromagnetic sensor.

The tip section 14 may also comprise an electromagnetic sensor connected to a system for monitoring and displaying the signals received from the sensor. The electromagnetic sensor allows a physician to identify the location of the catheter within the heart. A preferred electromagnetic sensor is manufactured by Biosense Ltd. Israel and marketed under the trade designation NOGA. A description of placement of an electromagnetic sensor in a steerable catheter is provided in U.S. patent application Ser. No. 08/924,616 entitled "Steerable Direct Myocardial Revascularization Catheter" to D. Ponzi, filed Sep. 5, 1997, the disclosure of which is incorporated herein by reference.

The catheter may, if desired, comprise an optic fiber for transmitting laser energy to heart tissue, for example, for a percutaneous myocardial revascularization procedure. A preferred means for incorporating an optic fiber into a steerable catheter is disclosed in U.S. Pat. No. 5,964,757, the disclosure of which is incorporated herein by reference.

Also, if desired, the catheter may comprise an infusion tube for infusing fluids, such as drugs or saline, into the heart or for withdrawing fluids from the heart. An infusion tube may extend through the central lumen of the catheter body and into the on-axis lumen in the tip section. The distal end of the infusion tube may extend into a passage in the tip electrode 110 and be fixed, e.g., by glue, to the tip electrode. Such a passage in the tip electrode may be straight or branched as desired. In such an embodiment, the proximal end of the infusion tube would extend out of a sealed opening in the side wall of the catheter body and terminates in a luer hub or the like as described in U.S. Pat. No. 5,431,168, which is incorporated herein by reference. Alternatively, the infusion tube may extend through the control handle and terminate in a luer hub or the like at a location proximal to the control handle.

In the embodiments described above, the central lumen 18 of the catheter body 12 is used for passage of the electrode lead wires 116 as well as the four puller wires 34, compression coils 36 and, if present, thermocouple wires, electromagnetic sensor cable, optic fiber or infusion tube. It is understood that the catheter body 12 could alternatively comprise a plurality of lumens. However, the single central lumen 18 is preferred because it has been found that a single lumen body permits better control when rotating the catheter 10. The single central lumen permits the puller wires 34, compression coils 36 and lead wires 110, as well as an optic fiber and or infusion tube to float freely within the catheter body 12. If such wires and tubes are restricted within multiple lumens, they tend to build up energy when the control handle 16 is rotated, resulting in the catheter body 12 having a tendency to rotate back if, for example, the handle is released, or if bent around a curve, to flip over, either of which are undesirable performance characteristics.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

I claim:

1. A bi-directional steerable catheter comprising:

an elongated catheter body having proximal and distal ends and at least one lumen therethrough;

a catheter tip section at the distal end of the catheter body having proximal and distal ends and at least two diametrically-opposed off-axis lumens;

a control handle at the proximal end of the catheter body, the control handle comprising at least four movable members movable between first and second positions;

two pairs of puller wires, each pair comprising associated long and short puller wires, each puller wire having proximal and distal ends, the proximal end being connected to an associated movable member of the control handle, each pair of puller wires extending through a lumen of the catheter body, each short puller wire extending into the proximal portion of a separate one of the diametrically opposed off-axis lumens in the tip section wherein the distal end of the short puller wire of each pair of puller wires is anchored to the tip section at a first position along the length of the tip section, each long puller wire extending through at least the portion of the tip section distal to the first position wherein the distal end of the long puller wire of each puller wire pair is anchored to the tip section at a position distal to the anchor position of its associated short puller wire;

a compression coil extending through the catheter body in surrounding relation to each puller wire, each compression coil having proximal and distal ends, the proximal ends of each compression coil being fixedly secured to the proximal end of the catheter body and wherein the distal ends of the compression coils in surrounding relation to the short puller wire of each puller wire pair is fixedly secured to one of the catheter body and tip section at a position proximal to the anchor position of the short puller wire to which it surrounds, and wherein the distal ends of the compression coil in surrounding relation to the long puller wire of each puller wire pair is fixedly secured to the tip section at a position proximal to the anchor position of the long puller wire to which it surrounds; and wherein movement of a movable member from its first to its second position results in proximal movement of the puller wire associated with that movable member relative to the catheter body.

2. A bi-directional catheter as claimed in claim 1, wherein the long puller wire of each puller wire pair is anchored at the distal end of the tip section.

3. A bi-directional catheter as claimed in claim 2, wherein the short puller wire of each puller wire pair is anchored at about the midpoint of the tip section.

4. A bi-directional catheter as claimed in claim 1, wherein the distal end of the compression coil in surrounding relation to each short puller wire is fixedly secured to one of the distal end of the catheter body and the proximal end of the tip section.

5. A bi-directional catheter as claimed in claim 4, wherein the distal end of the compression coil in surrounding relation to each long puller wire of each puller wire pair is fixedly secured to one of the distal end of the catheter body and the proximal end of the tip section.

6. A bi-directional catheter as claimed in claim 4 wherein the distal end of the compression coil in surrounding relation to the long puller wire of a puller wire pair is secured to the tip section a position along the length of the tip section adjacent the anchor position of the short puller wire of that puller-wire pair.

7. A bi-directional catheter as claimed in claim 1, further comprising means for preventing the movable member associated with the short puller wire of a puller wire pair from moving from its first to its second position when the movable member associated with the short puller wire of the other puller wire pair is in its second position and for preventing the movable member associated with the long puller wire of a puller wire pair from moving from its first to its second position when the movable member associated with the long puller wire of the other puller wire pair is in its second position.

8. A bi-directional catheter as claimed in claim 1, wherein the catheter body has a single lumen.

9. A bi-directional catheter as claimed in claim 1 comprising two diametrically opposed pairs of adjacent off-axis lumens and wherein each puller wire of a puller wire pair extends into a separate lumen of an adjacent off-axis lumen pair.

10. A bi-directional catheter as claimed in claim 1 wherein the tip section further comprises an axial lumen.

11. A bi-directional catheter as claimed in claim 10 wherein the tip section further comprises an axial lumen wherein each long puller wire extends into and through the axial lumen of the tip section and then, at or distal to the anchor position of its associated short puller wire, extends into and through the off axis lumen of its associated short puller wire.

12. A bi-directional catheter as claimed in claim 1, wherein the tip section carries at least one electrode.

13. A bi-directional catheter as claimed in claim 1, wherein the tip section carries at least one ring electrode.

14. A bi-directional catheter as claimed in claim 1, wherein the tip section carries a tip electrode.

15. A bi-directional catheter as claimed in claim 1, further comprising an infusion tube extending through a lumen in the catheter body and through a lumen in the tip section for passing a fluid through the catheter body and tip section.

16. A bi-directional catheter as claimed in claim 11, further comprising a means for sensing the temperature of at least one electrode.

17. A bi-directional catheter as claimed in claim 1, further comprising an electromagnetic sensor disposed within the tip section.

18. A bi-directional catheter as claimed in claim 1, further comprising an optic fiber extending though a lumen in the catheter body and through a lumen in the tip section.

19. A bi-directional catheter comprising:

an elongated catheter body having proximal and distal ends and at least one lumen therethrough;

a catheter tip section at the distal end of the catheter body having two diametrically opposed pairs of adjacent off-axis lumens;

a control handle at the proximal end of the catheter body, the control handle comprising at least four movable members that are movable between a first position and a second position;

two pairs of puller wires, each pair comprising associated long and short puller wires, each puller wire having proximal and distal ends and being attached at its proximal end to one of the movable members, wherein each puller wire of a puller wire pair extends through the lumen of the catheter body, and into one lumen of an off-axis lumen pair in the tip section, and wherein the short puller wires are anchored to the tip section along the length of the tip section and wherein the long puller wires are anchored to the tip section at a position distal to the anchor sites of its short puller wires at about the mid point of the tip section, a compression coil having proximal and distal ends extending through the lumen of the catheter body in surrounding relation to each puller wire, the proximal end of each compression coil being securely fixed to the proximal end of the catheter body and the distal end of the each compression coil is fixedly secured to one of the distal end of the catheter body or the proximal end of the tip section; and wherein movement of a selected movable member from its first position toward its second position results in deflection of a portion of the tip section in the direction of the off-axis lumen containing the puller wire associated with the selected movable member.

20. A bi-directional catheter as claimed in claim 19, wherein the anchor locations of the short puller wires is about the mid point of the tip section.

21. A bi-directional catheter as claimed in claim 19, wherein the catheter body has a single central lumen.

22. A bi-directional catheter as claimed in claim 19, wherein the distal end of each compression coil is anchored within the proximal end of the tip section.

23. A bi-directional catheter as claimed in claim 19, wherein the tip section further comprises an axial lumen.

24. A bi-directional catheter as claimed in claim 19, wherein the tip section carries at least one electrode.

25. A bi-directional steerable catheter comprising:

an elongated catheter body having proximal and distal ends and at least one lumen therethrough;

a catheter tip section at the distal end of the catheter body having proximal and distal ends and at least two diametrically-opposed off-axis lumens;

a control handle at the proximal end of the catheter body, the control handle comprising at least four movable members movable between first and second positions;

two pairs of puller wires, each pair comprising associated long and short puller wires, each puller wire having proximal and distal ends, the proximal end being connected to an associated movable member of the control handle, each pair of puller wires extending through a lumen of the catheter body, each short puller wire extending into the proximal portion of a separate one of the diametrically opposed off-axis lumens in the tip section wherein the distal end of the short puller wire of each pair of puller wires is anchored to the tip section at a first position along the length of the tip section, each long puller wire extending through at least the portion of the tip section distal to the first position wherein the distal end of the long puller wire of each puller wire pair is anchored to the tip section at a position distal to the anchor position of its associated short puller wire;

a compression coil extending through the catheter body in surrounding relation to each puller wire, each compression coil having proximal and distal ends, the proximal ends of each compression coil being fixedly secured to the proximal end of the catheter body and wherein the distal ends of the compression coils in surrounding relation to the short puller wire of each puller wire pair is fixedly secured to one of the catheter body and tip section at a position proximal to the anchor position of the short puller wire to which it surrounds, and wherein the distal ends of the compression coil in surrounding relation to the long puller wire of each puller wire pair is fixedly secured to the tip section at a position proximal to the anchor position of the long puller wire to which it surrounds; and wherein movement of a movable member from its first to its second position results in proximal movement of the puller wire associated with that movable member relative to the catheter body.

* * * * *